United States Patent
Medo

[11] Patent Number: 5,971,952
[45] Date of Patent: Oct. 26, 1999

[54] MANUAL BREAST PUMP

[76] Inventor: Elena M. Medo, 309 Escuela, San Clemente, Calif. 92672

[21] Appl. No.: 09/001,246

[22] Filed: Dec. 30, 1997

Related U.S. Application Data

[60] Provisional application No. 60/034,107, Dec. 30, 1996.

[51] Int. Cl.$^6$ ..................................................... A61M 1/06
[52] U.S. Cl. .............................................................. 604/74
[58] Field of Search .................................. 604/73, 74, 75, 604/346

[56] References Cited

U.S. PATENT DOCUMENTS

| | | |
|---|---|---|
| 883,158 | 3/1908 | Wallis . |
| 933,398 | 9/1909 | Stahl . |
| 4,772,262 | 9/1988 | Grant et al. . |
| 4,813,932 | 3/1989 | Hobbs ........................... 604/74 |
| 4,892,517 | 1/1990 | Yuan et al. ................... 604/74 |
| 5,009,638 | 4/1991 | Riedweg et al. ............. 604/74 |
| 5,749,850 | 5/1998 | Williams et al. ............. 604/74 |
| 5,843,029 | 12/1998 | Bachman et al. ............ 604/74 |

Primary Examiner—John D. Yasko
Attorney, Agent, or Firm—Stout, Uxa, Buyan & Mullins, LLP; Donald E. Stout

[57] ABSTRACT

A manual powered breast pump for efficiently removing milk from a patient's breasts which provides additional milk storage capacity. The breast pump includes an outer pumping cylinder, an inner pumping cylinder and pumping seal. The inner pumping cylinder or plunger is generally a hollow cylinder having a closed end and open end. The open end is fitted with a removable cap creating a secondary collection container. The plunger is also fitted with a seal for slidably contacting the interior wall of the hollow outer pumping cylinder. The outer pumping cylinder is fitted with a nipple for connection with a breast flange and an open end for collection with a collection container. A one-way valve is fitted within the outer pumping cylinder to provide for the efficient flow of milk into the collection container and to prevent the return of milk into the breast pump during pumping operations.

20 Claims, 3 Drawing Sheets

MANUAL BREAST PUMP

This application claims benefit of Provisional Application 60/034,107, filed Dec. 30 1996.

FIELD OF THE INVENTION

This invention relates generally to breast pumps and more particularly, to an improved manual powered breast pump.

BACKGROUND OF THE INVENTION

Breast pumps have long been used for removing milk from a lactating mother's breasts. These breast pumps include both powered and manual versions. In general, a manual breast pump consists of a plunger which freely slides within an outer cylinder. A seal is fitted around the outside of the plunger to seal against the inner surface of the outer cylinder. In this way, the plunger can slide within the outer cylinder to form a pump stroke. A breast flange or funnel is fluidly connected to the outer cylinder.

The mother applies suction to the breast by supporting the breast flange against the breast and pulling the plunger outwardly from the outer cylinder. Suction is created in the space which is expanded within the inside of the outer cylinder. The removed milk may be retained within the interior space of the outer cylinder or alternatively may be pumped out into a baby bottle or nurser bag which is connected to the outer cylinder.

These manual powered breast pumps of the prior art are often configured to be used with conventional baby bottles, collection containers or nursing bags. As discussed, these devices may be attached to the breast pump and function to contain the milk removed from the woman's breast. However, when using these containers, milk is often lost due to spillage or even leakage. This spillage can occur during pumping or when removing the filled container from the pump (outer cylinder), among other ways. In addition, differing collection containers can affect the performance of the breast pump by affecting the input orifice and venting, among other things. Thus, there is a need for a manual powered breast pump which may be utilized with a variety of different collection containers without affecting performance.

Often times, a woman using a conventional manual breast pump will produce and collect more milk than the collection bottle or nursing bag will hold. If the woman lacks an additional collection device, she must either discard the excess milk or refrain from pumping the excess breast milk. This incomplete removal of breast milk can be painful and may also lead to a reduction in future milk production. Carrying additional collection bottles or nursing bags is generally impractical due to their bulk. Thus, there is a need for a manual breast pump which provides additional collection space without necessitating increased size.

Additionally, a woman may desire to pump both breasts simultaneously. This allows the woman to recover a maximum amount of milk in a shorter period of time. Often this is accomplished using a powered breast pumping device. However, these devices are often only supplied with a single collection container. There is thus a need for a manual breast pump that can also be used as a second collection container in conjunction with another breast pumping device. Furthermore, it would be advantageous for such a manual breast pump to be compatible with most conventional powered breast pumping devices.

Therefore, a need exists for a manually powered breast pump which may be utilized with a variety of different collection containers without affecting the pumping or collection performance. Such a device is needed which could provide additional collection space without necessitating increased size of the pumping device and could be utilized with existing powered breast pumps. There is also a need for such a manually powered breast pump which is small in size, economical and simple to use.

SUMMARY

The present invention provides an improved manual powered breast pump which satisfies the need for a manual breast pump which may be used with most any conventional baby bottle, collection container or nursing bag without affecting pumping performance by providing a manually powered breast pump having a customized one-way valve. This valve allows pumped milk to flow into any collection container without the ability to flow back or leak into the pumping chamber. The valve is fitted inside the outer pumping cylinder so as to remain separate from and not affect the collection container.

The present invention also provides an improved manual powered breast pump which can handle the need for increased production without the disadvantage of increasing the overall pump size by providing a manually powered breast pump having a plunger which also acts as a reserve collection container. The plunger of the present invention is a hollow cylinder with one end closed and the other end fitted with exterior threads. A cap is fitted on the exterior threads to create a closable and sealable container. The threads are generally sized to fit a conventional baby bottle top.

The breast pump of the present invention also satisfies the need for a manual powered breast pump which may also be utilized as a second collection container when pumping both breasts. The cap of the present invention may be configured for use in conjunction with conventional powered breast pumps.

The present invention is generally directed to a manually powered breast pump which includes an outer pumping cylinder, an inner pumping cylinder or plunger, and a pump seal. The breast pump also includes a specialized one-way valve to allow for milk to be dispensed out of the pump and into a collection container and a flange or funnel for adapting to a woman's breasts without affecting pump performance.

The invention, together with the additional features and advantages thereof, will become more apparent to those of skill in the art upon reading the description of the preferred embodiments taken together with the following drawings.

BRIEF DESCRIPTION OF THE DRAWINGS

FIG. 3b is a cross-sectional view of the seal shown in FIG. 3a;

DESCRIPTION OF THE PREFERRED EMBODIMENTS

Figure 1:
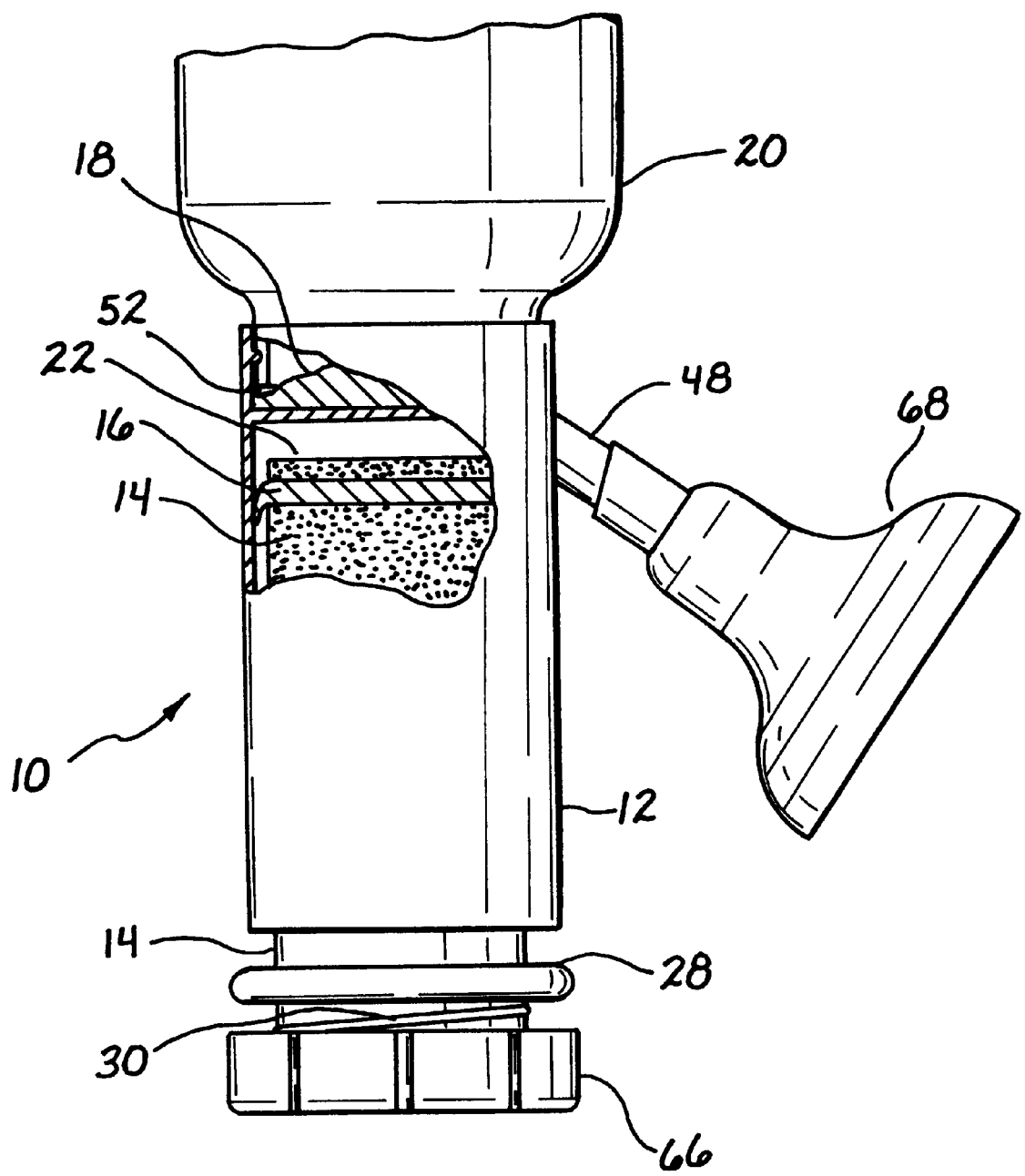
FIG. 1 is a perspective view of an embodiment of a breast pump of the present invention.

FIG. 1 illustrates an embodiment of a breast pump 10 of the present invention. The breast pump 10 includes an outer pumping cylinder 12, an inner pumping cylinder or plunger 14 and a pumping seal 16 disposed between the inner and outer cylinders 12 and 14. The breast pump also includes a one-way valve 18 mounted on the outer cylinder 12. A collection container 20 may be fitted onto the outer pumping cylinder for containing the pumped milk.

Figure 2A:
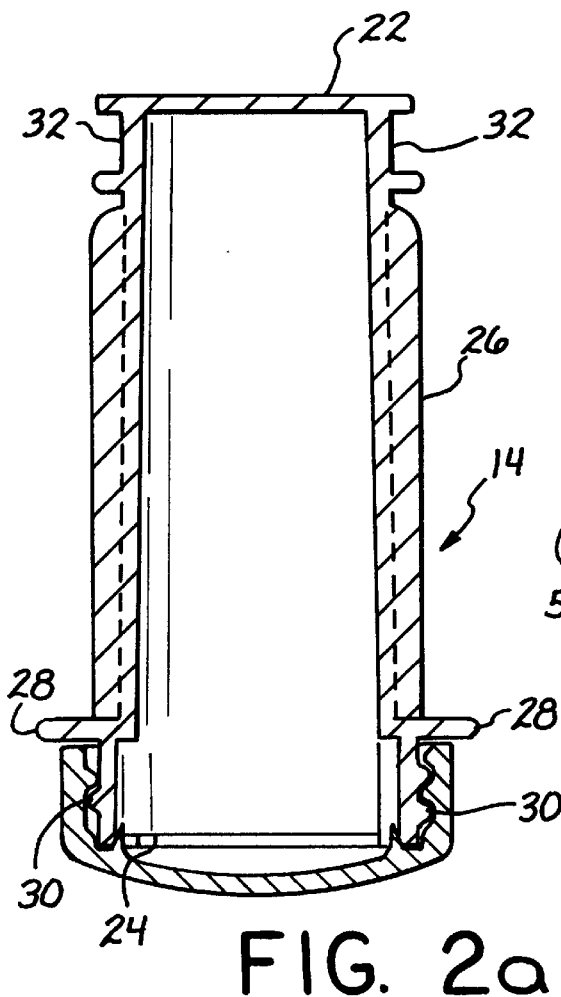
FIG. 2a is a cross-sectional view of the inner cylinder and cap of the breast pump as shown in FIG. 1.

Referring now to FIG. 2a the inner pumping cylinder or plunger 14 of the present invention will be described in greater detail. The plunger 14 is generally a hollow cylinder with a closed end or base 22 at one end and an open opposing end 24. The plunger 10 generally has a smooth outer surface 26 which provides generally frictionless contact with the outer cylinder 12. An annular ring or mechanical stop 28 may be provided which extends outwardly from the outer surface 26. External threads 30 are provided adjacent to the open end 24. An annular groove or slot 32 is provided adjacent to the base end 22.

Figure 2B:
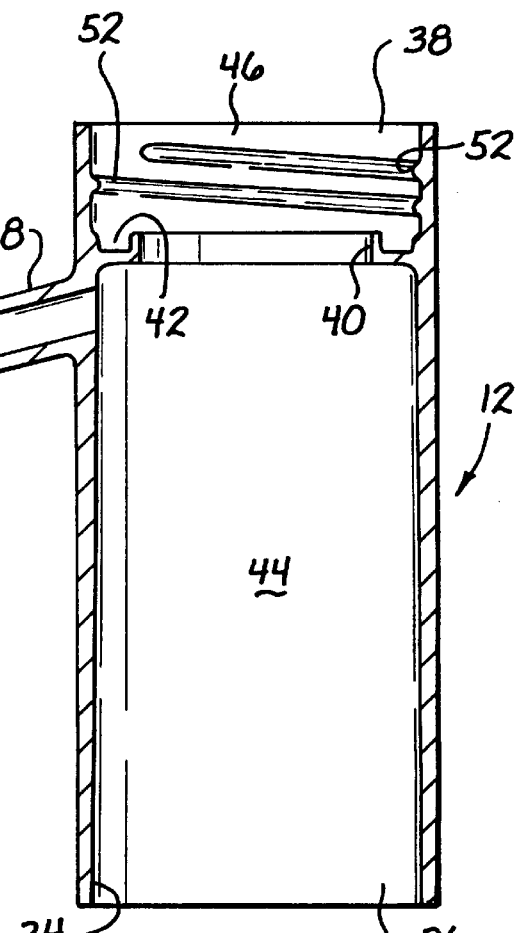
FIG. 2b is a cross-sectional view of the outer cylinder of the breast pump as shown in FIG. 1.

FIG. 2b shows the outer pumping cylinder 12 in greater detail. The outer pumping cylinder 12 is generally a hollow cylinder having an interior wall 34, an open first end 36 and an open second end 38. An interior annular ring 40 projects inwardly from the hollow interior wall 34 to form an annular groove 42. The annular ring 40 separates the outer pumping cylinder 12 into a first pumping chamber 44 and a second pumping chamber 46. A nipple 48 extends outwardly from the outer pumping cylinder 12 and has a passageway 50 connecting the first pumping chamber 44 to the exterior of the outer pumping cylinder 12. The interior wall 34 of the second pumping chamber 46 may be fitted with interior threads 52 or other fastening grooves or means as is known in the art.

Figure 3A:
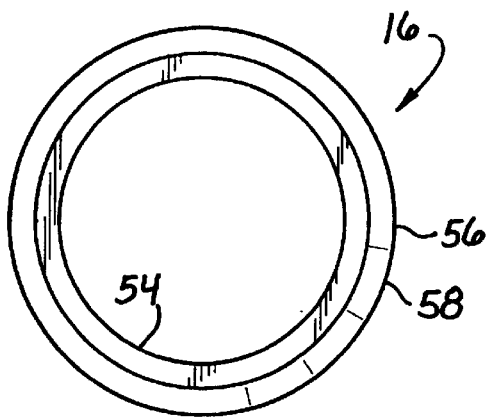
FIG. 3a is a top view of an embodiment of a seal used in the present invention.
Figure 3B:
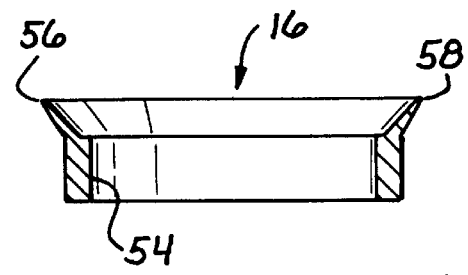

Referring now in particular to FIGS. 3a and 3b, the pumping seal 16 of the present invention is illustrated. The pumping seal 16 includes an inner diameter 54 and a rim 56 which defines the outer diameter 58. The pumping seal 16 is generally designed to fit within the annular groove or slot 32 of the plunger 14. The rim 56 generally has an outwardly tapered surface for contacting the interior wall 34 of the outer cylinder 12. In this way, the pumping seal 16 provides a generally fluid-tight seal between the interior wall 34 of the outer pumping cylinder 12 and the plunger 14. The pumping seal 16 may be made from any material which is flexible, durable and non-toxic, such as seals commonly used in the food and milk industries.

Figure 4A:
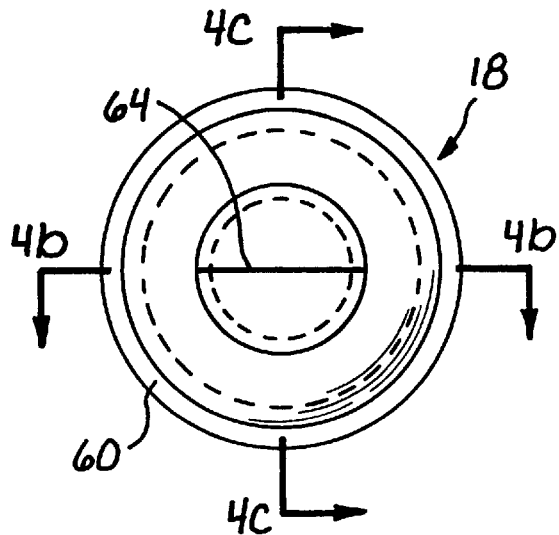
FIG. 4a is a top view of an embodiment of a one-way valve of the present invention.
Figure 4B:
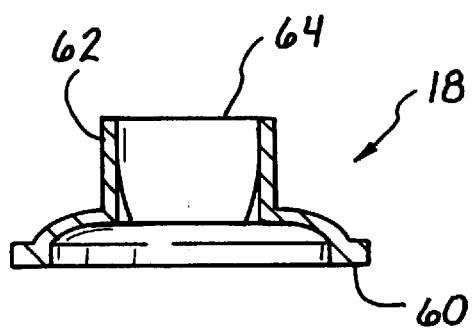
FIG. 4b is a cross-sectional view of the one-way valve shown in FIG. 4a taken along lines b—b.
Figure 4C:
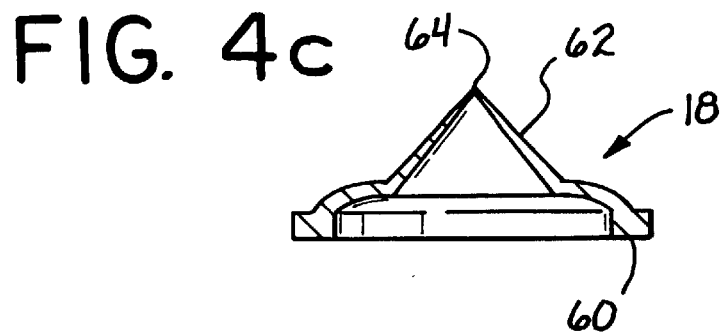
FIG. 4c is a cross-sectional view of the one-way valve as shown in FIG. 4a taken along lines c—c.

FIGS. 4a, 4b and 4c, show an embodiment of the one-way valve 18 of the present invention which will be described in greater detail. The one-way valve 18 is generally a single piece valve made from a flexible material. Similar to the pumping seal 16, the one-way valve 18 is preferably made from a material which is flexible, durable, non-toxic and very compatible with milk. The one-way valve 18 generally has a flat lower surface defining an outer rim 60 which narrows into a duck bill valve 62 having a slit 64. In this way, milk can enter through the outer rim 60 and pass through the slit 64 of the duck bill valve 62, but cannot return through the slit 64 of the duck bill valve 62.

The one-way valve 18 is generally configured to fit within the second pumping chamber 46 of the outer cylinder 12. Specifically, the outer rim 60 may be sized to fit within the annular groove 42. This fit may require stretching the outer rim to form a snug-tight fit within the annular groove 42. The fit preferably acts to retain the one-way valve 18 in the second pumping chamber 18 and prevents the leakage of milk under the outer rim 60. The height of the duck bill valve 62 may be limited such that the one-way valve 18 generally does not extend out of the second pumping chamber 46. In this way, the one-way valve 18 is less likely to be knocked off or otherwise dislodged when removing or connecting a collection container.

Referring now back to FIG. 1, the manual breast pump 10 of the present invention will be described in greater detail including its operation. Broadly speaking, the plunger 14 is inserted inside the outer pumping cylinder 12. The plunger 14 may be made from any material which is durable, non-toxic, compatible with milk and generally has a frictionless outer surface 26. Preferably, the plunger 14 may be made from a plastic. The plunger 14 may be fitted with the pumping seal 16 within the annular slot 32. The pumping seal 16 provides a seal between the plunger 14 and the inner wall 34 of the outer cylinder 12. The stop 28 may be provided on the outer surface 26 to prevent over insertion of the plunger 14 into the outer pumping cylinder 12. This stop may be a mechanical stop such as an outwardly extending annular ring 28. However, any means of mechanically preventing the plunger 14 from being over inserted into the outer pumping cylinder 12 may be used. A cap 66 is removably fitted over the open end 24. In this way, the plunger 14 is also a container having a removable cap 66. To provide increased utility, the cap 66 may be fitted on the plunger 14 through use of the external threads 30. These external threads 30 may preferably be sized to fit a conventional baby bottle or other collection container. Other means of securing the cap 66 to the plunger 14 as are commonly known, may also be used. The cap 66 may also be fitted with various devices for filling and venting the interior of the plunger 14 as are known in the art of filling containers.

The outer cylinder 12 generally includes an outwardly protruding nipple 48 or other coupling device. A breast flange or funnel 68 may be fitted to the nipple 48 to provide an apparatus for removing milk from the woman's breasts and transporting it into the breast pump 10. The nipple 48 preferably has an outer diameter suitable for use with conventional breast flanges 68, such as the SOFT-CUP™ breast flange sold by White River Concepts, Inc. of San Clemente, Calif., which is the subject of U.S. Pat. No. 4,772,262. Alternatively, the nipple 48 may be connected to a tubing or other device for connection with the breast flange 68 or the woman's breast. In this way, the pump 10 may be actuated while being supported away from the patient's breast.

The outer pumping cylinder 12 may be made from a material, like the plunger 14, which is also durable, non-toxic, and compatible with milk. The outer cylinder 12 preferably has a smooth interior wall 34 for smooth operation with the seal 16 and the outer wall of the plunger 14.

The one-way valve 18 may be fitted into the second pumping chamber 46 of the outer pumping cylinder 12 to allow passage of the pumped milk into a collection container 20. In general, the one-way valve 18 is provided with a single orifice having a single slit 64. However, any type of one-way valve that provides smooth passage of milk from the first pumping chamber 44 into a collection container without allowing the milk to return through the valve may be used.

A collection container 20 is fitted onto the outer pumping cylinder 12. More specifically, the collection container 20 which may be a baby bottle, a nursing bag or any other type of collection container for use with milk may be attached to the second end 38 of the outer pumping cylinder 12 using any method of fastening which prevents leakage as well as the formation or ingress of contamination. Preferably the collection container 20 is fitted with exterior threads which mate with the interior threads 52 of the second pumping chamber 46. In this way, the collection container may be threaded into the second pumping chamber 46 creating a simple to install and leak proof connection. These interior threads 52 are preferably sized to mate with a conventional baby bottle or other collection container 20.

In operation, a collection container 20 is connected to the second end 38 of the outer pumping cylinder 12. A breast flange or funnel 68 is fitted over or otherwise connected to the nipple 48. The plunger 14 is fitted with the pumping seal 16 and inserted into the outer pumping cylinder 12. A removable cap 66 is fitted onto the open end 24 of the plunger 14 to prevent the ingress of contamination.

The breast flange 68 is then secured against the woman's breasts while the outer pumping cylinder 12 is held firmly. The plunger 14 is pulled outwardly from the outer pumping cylinder 12 creating a suction in the breast flange 68. This suction withdraws milk from the patient's breasts which is transferred through the passageway 50 in the nipple 48 and into the first pumping chamber 44. The plunger 14 is then pushed back into the outer pumping cylinder 12 while the breast flange 68 is held secured against the patient's breasts. In this way, the milk in the first pumping chamber 44 is forced into the second pumping chamber 46 through the one-way valve 18 and into the collection container 20. The process is then repeated with the plunger 14 being pulled outwardly from the outer pumping cylinder 12. The one-way valve 18 prevents milk within the collection container 20 from being drawn into the outer pumping cylinder 12.

Once the collection container 20 is filled, the patient may stop pumping operation, remove the collection container 20 from the outer pumping cylinder 12 and well as the removable cap 66 from the plunger 14, and fill the hollow interior of the plunger 14 with milk from the container 20. After the plunger 14 is filled, the removable cap 66 is replaced. In this fashion, milk from the collection container 20 is poured into the plunger 14 making addition space available in the collection container 20 and allowing for additional removal of milk from the patient's breasts.

Alternatively, the removable cap 66 may be removed from the plunger 14 providing a container which may be filled with milk being simultaneously pumped from the patient's opposing breast. In this way, both breasts may be pumped simultaneously. The cap 66 may be fitted with various devices to facilitate the filling of the plunger 14 without having to remove the plunger 14 from the outer pumping cylinder 12.

While this invention has been described with respect to various examples and embodiments, it is to be understood that the invention is not limited thereto.

What is claimed is:

1. A breast pump, comprising:

an outer cylinder having a cylindrical wall;

an inner cylinder having a cylindrical wall and being slidably disposed telescopically within said outer cylinder to form a plunger, the inner cylinder having a first closed end and a second open end; and a removable cap disposed on said inner cylinder open end, for closing said open end so that the inner cylinder wall defines an enclosed interior volume.

2. The breast pump as recited in claim 1, and further comprising a pumping seal disposed between the inner cylinder wall and the outer cylinder wall.

3. The breast pump as recited in claim 1, and further comprising threads disposed on said inner cylinder wall at said open end for threaded engagement with said removable cap.

4. The breast pump as recited in claim 1, and further comprising a collection container attached to said outer cylinder.

5. The breast pump as recited in claim 4, and further comprising a one-way valve disposed in said outer cylinder between said collection container and said inner cylinder.

6. The breast pump as recited in claim 5, wherein said one-way valve comprises a duckbill valve.

7. The breast pump as recited in claim 6, wherein said outer cylinder further comprises an annular ring projecting inwardly from said outer cylinder wall to divide said outer cylinder into a first pumping chamber and a second pumping chamber.

8. The breast pump as recited in claim 7, said annular ring having an annular groove formed thereon, said one-way valve having an outer rim which is sized to snugly fit into said annular groove, such that the oneway valve is securely retained in said second pumping chamber.

9. The breast pump as recited in claim 1, wherein said inner cylinder includes an annular stop projecting outwardly from an outer surface of the cylindrical wall thereof adjacent to said second open end, for preventing overinsertion of said inner cylinder into said outer cylinder.

10. The breast pump as recited in claim 1, wherein said inner cylinder includes an annular groove disposed on an outer surface of the cylindrical wall thereof adjacent to said first closed end for receiving and securing portions of said pumping seal.

11. The breast pump as recited in claim 7, and further comprising internal threads disposed in said second pumping chamber, for mating with corresponding threads on a milk collection container, thereby attaching said container to said outer cylinder.

12. A breast pump, comprising:

an outer cylinder having a cylindrical wall;

an inner cylinder having a cylindrical wall and being slidably disposed telescopically within said outer cylinder to form a plunger;

said inner cylinder including an interior volume defined by said inner cylinder wall which is fillable with liquid through a selectively closable opening disposed on said inner cylinder.

13. The breast pump as recited in claim 12, wherein said inner cylinder comprises a first closed end and a second open end, the second open end comprising said selectively closable opening, the breast pump further comprising a removable cap for selectively closing the second open end.

14. The breast pump as recited in claim 12, and further comprising threads disposed on said inner cylinder wall at said open end for threaded engagement with said removable cap.

15. The breast pump as recited in claim 12, and further comprising a collection container attached to said outer cylinder.

16. The breast pump as recited in claim 15, and further comprising a one-way valve disposed in said outer cylinder between said collection container and said inner cylinder.

17. The breast pump as recited in claim 16, wherein said one-way valve comprises a duckbill valve.

18. A breast pump, comprising:
- an outer cylinder having a cylindrical wall and having a first pumping chamber and a second pumping chamber;
- an inner cylinder having a cylindrical wall and being slidably disposed telescopically within said outer cylinder to form a plunger;
- a collection container attached to said outer cylinder; and
- a one-way valve disposed in said second pumping chamber between said collection container and said inner cylinder.

19. The breast pump as recited in claim 18, wherein said one-way valve comprises a duckbill valve.

20. The breast pump as recited in claim 19, wherein said outer cylinder further comprises an annular ring projecting inwardly from said outer cylinder wall to divide said outer cylinder into said first and second pumping chambers, said annular ring having an annular groove formed thereon, said one-way valve having an outer rim which is sized to snugly fit into said annular groove, such that the one-way valve is securely retained in said second pumping chamber.

* * * * *